United States Patent [19]

Kassai

[11] Patent Number: 4,861,405
[45] Date of Patent: Aug. 29, 1989

[54] METHOD AND APPARATUS FOR APPLYING BABY POWDER TO DISPOSABLE DIAPERS

[75] Inventor: Kenzou Kassai, Osaka, Japan

[73] Assignee: Aprica Kassai Kabushikikaisha, Osaka, Japan

[21] Appl. No.: 218,320

[22] Filed: Jul. 12, 1988

[30] Foreign Application Priority Data

Jul. 13, 1987 [JP] Japan .................. 62-174418

[51] Int. Cl.$^4$ ............................................. B32B 31/12
[52] U.S. Cl. .................................... 156/204; 118/308; 118/612; 156/216; 156/276; 156/324; 427/202; 428/129; 428/206; 604/367
[58] Field of Search ............... 118/308, 612; 156/204, 156/216, 276, 324; 427/180, 202; 428/126, 129, 206; 604/367

[56] References Cited

U.S. PATENT DOCUMENTS 4,627,990 12/1986 Saga et al. ..................... 427/180 X
4,753,643 6/1988 Kassai .

FOREIGN PATENT DOCUMENTS 13701 1/1983 Japan .
13704 1/1983 Japan .

*Primary Examiner*—Robert A. Dawson
*Attorney, Agent, or Firm*—W. G. Fasse; D. H. Kane, Jr.

[57] ABSTRACT

A laminated continuous sheet which, when cut, forms individual disposable diapers is moved at high speed in the direction of the length thereof, whereby in an air zone of predetermined thickness disposed on at least a predetermined surface of the laminated continuous sheet, there is produced with the travel of the laminated continuous sheet an air flow having a velocity gradient such that the speed of the air flow increases as the predetermined surface is approached. Baby powder is fed at a position within the air zone of predetermined thickness so that it contacts the air zone. By utilizing a decreasing-pressure phenomenon produced by the air flow having a velocity gradient described above in which the pressure decrease as the predetermined surface of the laminated continuous sheet is approached, baby powder is caused to adhere to the predetermined surface as it is drawn toward the predetermined surface of the laminated continuous sheet.

10 Claims, 2 Drawing Sheets

METHOD AND APPARATUS FOR APPLYING BABY POWDER TO DISPOSABLE DIAPERS

FIELD OF THE INVENTION

The present invention relates to a method and an apparatus for applying baby powder to disposable diapers.

BACKGROUND INFORMATION

A disposable diaper is generally formed of an inner member to be in contact with the skin of a baby or sick person, an outwardly directed outer member and an absorbent member interposed therebetween. Generally, a water-permeable nonwoven fabric is used for the inner member and a waterproof film for the outer member. Such conventional disposable diapers have come into wide use in recent years, and manufacturers of disposable diapers have made various studies for improving the material and structure thereof.

On the other hand, it has been practiced to apply baby powder each time the diaper is changed. The purpose is to protect against miliaria and diaper rash. Further, baby powder contains a suitable perfume, having the effect of destroying a bad smell given off from the egesta from babies or sick persons.

However, application of baby powder each time the diapers is changed is relatively troublesome since said application makes it necessary to keep baby powder at hand at all times and increases the time taken to change the diaper.

DESCRIPTION OF THE RELATED ART

Accordingly, the applicant has previously proposed a disposable diaper having baby powder retained thereon as it is or in its pulverulent form in advance, in his copending U.S. Pat. No. 4,753,643, issued on June 28, 1988 entitled "Disposable Diaper". Such baby powder will be most effective if it is retained on the inner member of a disposable diaper.

In order to implement of the aforementioned related technique, there is required a technique for applying baby powder to disposable diapers in relation to the manufacture of disposable diapers.

The aforementioned copending application also discloses a technique for applying baby powder to disposable diapers.

SUMMARY OF THE INVENTION

Accordingly, the present invention is intended to provide a method and an apparatus for applying baby powder to disposable diapers so as to provide a disposable diaper having baby powder retained thereon in advance as described above.

In order to solve the aforementioned technical problem, the method according to the present invention comprises the steps of:

(a) moving a laminated continuous sheet, which, when cut, is to become individual disposable diapers, at high speed in the direction of the length thereof, whereby in an air zone of predetermined thickness disposed on at least a predetermined surface of the laminated continuous sheet, there is produced an air flow hving a velocity gradient such that the speed of the air flow increases as said predetermined surface is approached, (b) feeding baby powder at a position within said air zone of predetermined thickness in which said air flow is produced, so that the baby powder thus fed contacts said air zone, (c) making use of a decreasing-pressure phenomenon resulting from said air flow having said velocity gradient in which phenomenon the pressure decreases as said predetermined surface is approached, whereby said baby powder is caused to adhere to said predetermined surface of said laminated continuous sheet as it is drawn toward said predetermined surface.

In order to solve the aforementioned technical problem, an apparatus of the present invention comprises:

(a) conveyor device for moving a laminated continuous sheet, which, when cut, is to become individual diposable diapers, at high speed in the direction of the length thereof, whereby in an air zone of predetermined thickness disposed on at least a predetermined surface of the laminated continuous sheet, there is produced an air flow having a velocity gradient such that the speed of the air flow increases as said predetermined surface is approached, (b) a storage source for storing baby powder, (c) a delivery device for delivering said baby powder from said storage source by predetermined amount per unit time, (d) a feed path connected to said delivery device for guiding said baby powder delivered therefrom, said feed path being disposed to extend into said air zone of predetermined thickness in which said air flow is produced, said feed path having an outlet located in said air zone.

The method and apparatus according to the invention have a starting point based on the facts that in mass-production of disposable diapers, the row material takes the form of a laminated continuous sheet before it is cut into individual disposable diapers and that such laminated continuous sheet is subjected to various processes while it is being moved in the direction thereof at high speed. That is, it will be understood that if the row material is moved at high speed while taking the form of a laminated continuous sheet, an air flow is produced with the travel of the laminated continous sheet. More particularly, in an air zone of predetermined thickness disposed on at least at predetermined surface of the laminated continuous sheet being moved, as a necessary consequence of the travel of the laminated continuous sheet there is produced an air flow having a velocity gradient such that because of the velocity of air the speed of the air flow increases as said predetermined surface is approached. Such air flow having said velocity gradient results in a phenomenon in which the air pressure becomes lower as said predetermined surface is approached. Therefore, if, at a position within said air zone of predetermined thickness in which an air flow is produced in said manner, baby powder is fed so that it contacts said air zone, the baby powder will be forced to be drawn toward said predetermined surface of the laminated continuous sheet; thus, the baby powder is caused to adhere to said predetermined surface of the laminated continuous sheet.

According to the method of the present invention utilizing such actions, high efficiency can be attained since application of baby powder is performed when the row material is still in the form of a laminated continuous sheet previous to being cut into individual disposable diapers. Furthermore, such laminated continuous sheet form must be necessarily taken in the process of production of disposable diapers. Further, moving such laminated continuous sheet at high speed has been common practice in the manufacture of diposable diapers which must be mass-produced. Generally, the laminated continuous sheet is moved in the direction of the length thereof at speeds between 2.0 and 2.5 m/sec or thereabouts. For these reasons, in embodying the method of the invention there is no need for making a drastic change in the conventional manufacturing method; it is only necessary to add a step for applying baby powder. Therefore, the method according to the invention can be relatively easily employed.

Further, in the method of the invention, there is no need for providing special energy in implementing the step of feeding baby powder and the step of causing baby powder to adhere. The reasons are that, as previously described, it has been common practice to move the laminated continuous sheet at high speed in the process of mass-production of disposable diapers and that an air flow which is necessarily produced with the travel of the laminated continuous sheet is used as the energy for moving baby powder until it adheres to the laminated continuous sheet.

Further, the air flow described above has a velocity gradient such that its speed increases as the predetermined surface is approached; therefore, if the position at which baby powder is fed to contact the air zone is moved closer to the predetermined surface of the laminated continuous sheet, a greater force will act on the baby powder, causing a greater amount of baby powder to adhere to the laminated continuous sheet. Reversely, as the location in question becomes more distant from the predetermined surface of the laminated continuous sheet; the suction force on the baby powder decreases and hence a smaller amount of baby powder adheres to the laminated continuous sheet. In this way, the amount of baby powder which adheres can be adjusted by changing the baby powder feed position in the air zone of predetermined thickness in which the air flow is produced.

The speed of the air flow produced with the travel of the laminated continuous sheet is approximately proportional to the traveling speed of the laminated continuous sheet. Considering the relation between the traveling speed of the laminated continuous sheet and the required amount of baby powder fed per unit time, it is seen that when it is desired to make constant the amount of baby powder which adheres per unit area of the laminated continuous sheet, the amount of baby powder fed per unit time must be increased the more, the higher the traveling speed of the laminated continuous sheet. Since the method of the invention includes the step of feeding baby powder at a position in the air zone in which the air flow is produced so that it contacts the air zone, the amount of baby powder fed in this step is approximately proportional to the size of decrease in pressure caused by the air flow. Therefore, if the traveling speed of the laminated continuous sheet is increased, the amount of baby powder fed per unit time will increase and, reversely, if the traveling speed of the laminated continuous sheet is decreased, the amount of baby powder fed per unit time will decrease. This means that eventually the amount of baby powder adhering to the laminated continuous sheet per unit area thereof is automatically controlled so that it is constant irrespective of the traveling speed of the laminated continuous sheet.

According to the apparatus of the present invention, it is only necessary to dispose the outlet of the feed path in the vicinity of the laminated continuous sheet to which baby powder is to be applied, in addition to securing the effects provided by the aforementioned method of the invention. This disposition does not require a large space. Therefore, such apparatus or feed path can be advantageously installed by utilizing the small space left in the conventional equipment for manufacturing disposable diapers. Thus, the conventional equipment can be utilized as it is.

According to the apparatus of the invention, the provision of a delivering device for delivering a predetermined amount of baby powder per unit time from a storage source makes it possible to control the amount of baby powder which ultimately adheres to the laminated continuous sheet by adjusting the amount of baby powder to be delivered from said delivering device.

These objects and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
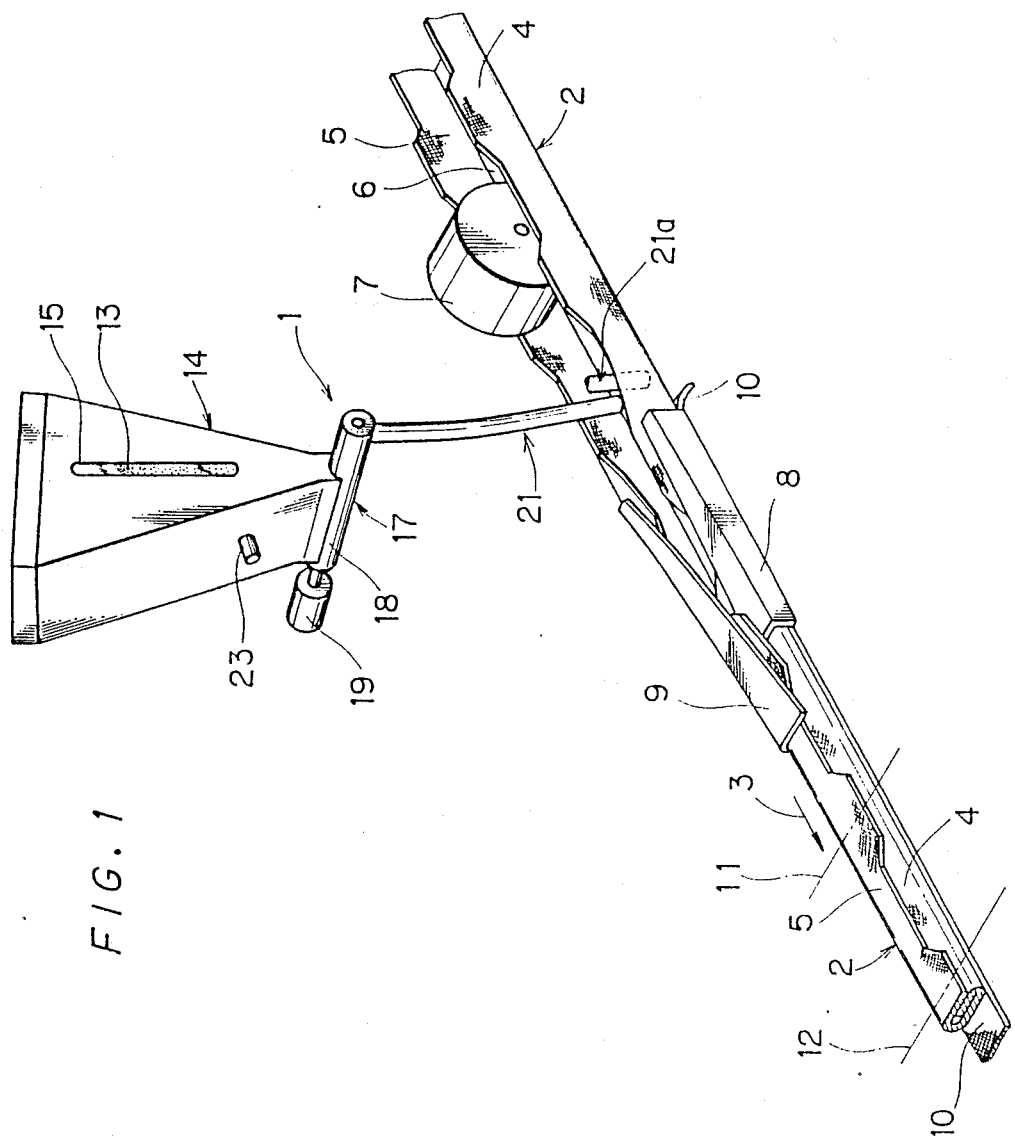
FIG. 1 is a perspective view showing the external appearance of a baby powder applying device 1 according to an embodiment of the invention, illustrating the positional relation to a traveling laminated continuous sheet 2 as well.

FIG. 1 is a perspective view of an apparatus according to an embodiment of the invention. A baby powder applying device 1 shown in FIG. 1 is designed to be added to a part of an apparatus for manufacturing disposable diapers described in Japanese Patent Application Laying-Open Gazette No. 13701/1983 or 13804/1983.

As shown in FIG. 1, the process for manufacturing disposable diapers includes a step for forming a laminated continuous sheet 2 comprising an inner member, an absorbent member and an outer member, previous to providing disposable diapers such as described above. While the laminated continuous sheet 2 is traveling in the direction or arrow 3, it goes successively through various working steps. The state shown in FIG. 1 corresponds substantially to the final step in such manufacturing process, showing a step for bending said laminated continuous sheet which is performed previous to the step of cutting said laminated continuous sheet into individual disposable diapers. That is, in the bending step, two opposite lateral edges 4 and 5 are bent so that a predetermined surface 6, or more particularly the surface on which the inner member lies is inwardly directed.

As shown in FIG. 1, the laminated continuous sheet 2 is conveyed with its predetermined surface 6 directed upward. A rotary drum 7 whose axial length is less than the width of the laminated continuous sheet 2 is pressed against the predetermined surface, whereby the opposite lateral edges 4 and 5 are raised. In addition, the rotary drum 7 may be replaced by a fixedly installed pressing member whose width is equal to the axial length of the rotary drum 7.

The laminated continuous sheet 2 passing under the rotary drum 7 is led to a pair of bending guides 8 and 9. Each of the bending guides 8 and 9 is L- or U-shaped, so that when the laminated continuous sheet 2 is passed through these bending guides 8 and 9, it is forcibly conveyed as it is supported by a conveyor belt 10 which s introduced from below. One bending guide 8 is located upstream of the other bending guide 9, as viewed in the direction of travel of the laminated continuous sheet 2. Therefore, the laminated continuous sheet 2 is bent first along one lateral edge 4 by one bending guide 8 and then along the other lateral edge 5 by the other bending guide 9. After the laminated continuous sheet 2 has passed through these bending guides 8 and 9, its state is such that one lateral edge 4 underlies the other lateral edge 5 while the predetermined surface 6 is completely or substantially completely hidden.

In addition, the laminated continuous sheet 2 which has thus been bent is then cut at positions shown in dot-dash lines 11 and 12, whereby individual disposable diapers are produced.

In this embodiment, the baby powder applying device 1 is disposed between the rotary drum 7 and the bending guides 8 and 9. The baby powder applying device 1 is installed preferably in the vicinity of each of the lateral edges 4 and 5 of the laminated continuous sheet 2. In addition, in FIG. 1, one baby powder applying device 1 alone is shown to indicate its entire external appearances and a sectional view of this baby powder applying device 1 is shown in FIG. 2.

Figure 2:
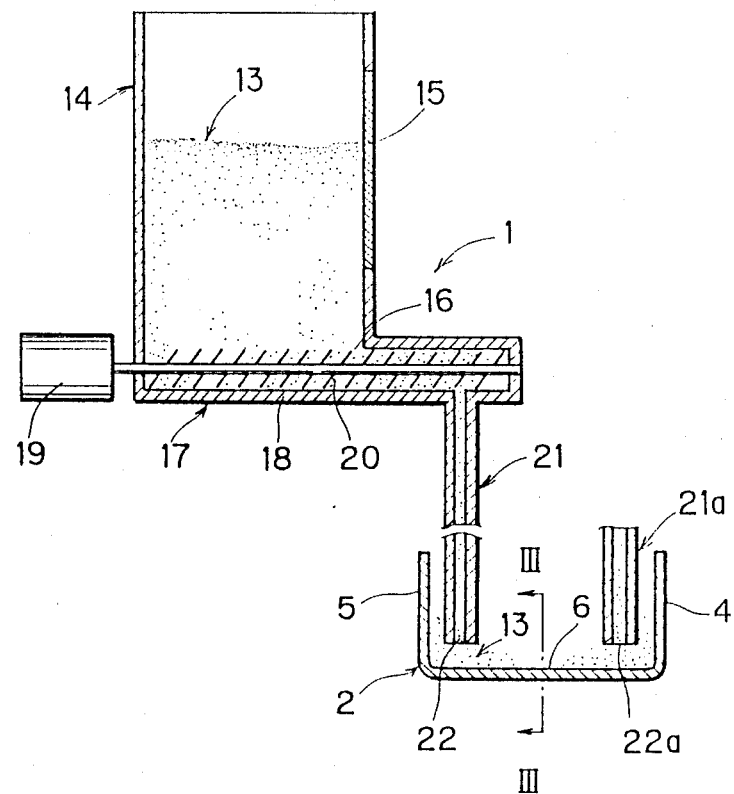
FIG. 2 is a sectional view of the baby powder applying device 1 shown in FIG. 1.

Referring to FIGS. 1 and 2, the baby powder applying device 1 includes a hopper 14 serving as a storage source for storing baby powder 13. The hopper 14 is in the form of an inverted triangle as a whole, and is formed with a vertically extending see-through window 15 through which the behavior of the baby powder 13 and the remaining amount thereof can be seen from outside. An opening 16 is formed in the lower end of the hopper 14.

Connected to the lower end of the hopper 14 is a screw feeder 17 serving as a delivering device for delivering the baby powder 13 by a predetermined amount per unit time. The screw feeder 17 has a cylindrical trough 18 whose interior communicates at one of its longitudinal ends with the space of the hopper 14. A screw 20 adapted to be rotated by a motor 19 is installed in the trough 18. The rotation of the screw 20 moves the baby powder 13 to the right as viewed in FIG. 2.

The screw feeder 17 has connected thereto a tubular conduit 21 serving as a feed path for guiding the baby powder 13 further downward. The conduit 21 is connected to the right-hand side of the trough 18 in FIG. 2. the conduit 21 extends vertically as a whole and has an outlet 22 in the lower end thereof. Preferably the outlet 22 is positioned adjacent one lateral edge 5 and not spaced very far from the predetermined surface 6 of the laminated continuous sheet 2.

In addition, the surfaces of the baby powder applying device 1 comprising the hopper 14, screw feeder 17 and conduit 21 which are in contact with the baby powder 13 preferably have an anti-static treatment applied thereto to prevent undesired sticking of the baby powder 13 due to generation of static charge.

Further, as shown in FIG. 1, it is desirable to attach a vibrator 23 to the hopper 14, for example. The vibrator 23 imparts vibration to the baby powder 13 to enhance smooth movement of the latter. In addition, if the vibrator 23 is attached at the position illustrated in FIG. 1, the vibrations produced thereby will be applied not only to the hopper 14 but also to the screw feeder 17 and conduit 21. Therefore, a smooth movement of the baby powder 13 can be expected.

In FIGS. 1 and 2, a part of the other conduit 21a is shown. This conduit 21a forms a part of the other baby powder applying device, not shown. This baby powder applying device has the same construction as the illustrated baby powder applying device 1. The conduit 21a has its outlet 22a positioned in the vicinity of the other lateral edge 4.

An embodiment of the baby powder applying method will now be described together with the operation of the baby powder applying device 1.

When the screw feeder 17 in the baby powder applying device 1 is driven by the motor 19, the screw 20 is rotated. With this rotation of the screw 20, the baby powder 13 is fed by a predetermined amount per unit time from the hopper 14 into the conduit 21 via the trough 18. The baby powder 13 reaching the conduit 21 is discharged from the outlet 22 substantially by gravity.

The reason for using the words "substantially by gravity" is that the force which guides the baby powder 13 to the outlet 22 has a gravity component and another component, as will become apparent from the following description.

Figure 3:
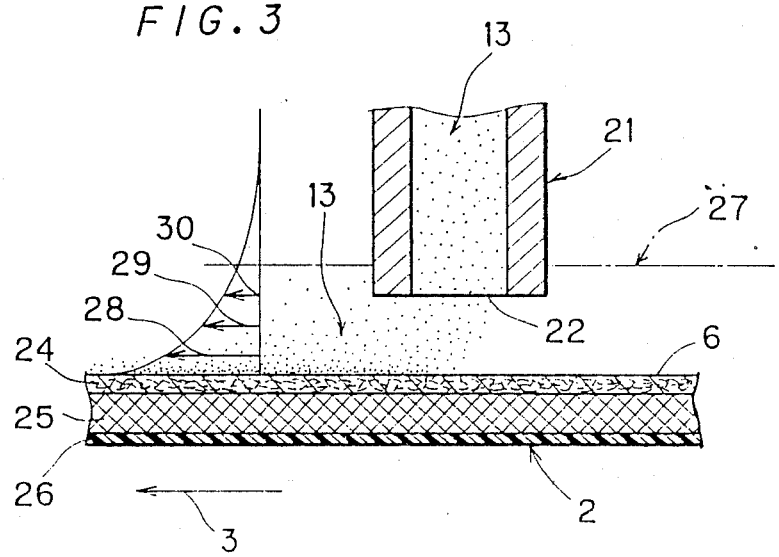
FIG. 3 is an enlarged sectional view taken along the line III—III in FIG. 2.

The outlet 22 of the conduit 21 is directed to the predetermined surface 6 of the laminated continuous sheet 2, as described above. The same is true of the outlet 22a of the other conduit 21a. On the other hand, the laminated continuous sheet 2 is conveyed in the direction of arrow 3. In addition, the traveling speed of the laminated continuous sheet 2 is about 2.0–2.5 m/sec, for example. When the laminated continuous sheet 2 is traveling at high speed, there is produced a non-negligible influence on the surrounding air. The present invention is characterized by advantageously utilizing this non-negligible influence on the air. This will now be described with reference to FIG. 3. FIG. 3 is an enlarged sectional view taken long the line III—-III in FIG. 2.

In FIG. 3, the laminated continuous sheet 2 is shown having a three-layer construction comprising an inner member 24, an absorbent member 25 and an outer member 26. The laminated continuous sheet 2 is traveling at high speed in the direction of arrow 3 (corresponding to the arrow 3 in FIG. 1), whereby in an air zone 27 of predetermined thickness disposed on the predetermined surface 6 of the laminated continuous sheet 2 there is produced with the travel of the laminated continuous sheet 2 an air flow as indicated by arrows 28, 29 and 30. These arrows 28, 29 and 30 are expressed as vectors indicating the velocities of the air flow included in the air zone 27. As can be seen from the lengths of these arrows, in the air zone 27 there is produced an air flow having a velocity gradient such that as a result of the viscosity the speed of the air flow increases as the predetermined surface 6 is approached.

The aforementioned conduit 21, as shown in FIG. 3, is disposed so that it projects into the air zone 27, with its outlet 22 positioned in the air zone 27. Therefore, the baby powder 13 being transferred through the conduit 21 is fed to the air zone 27 at a predetermined position therein so that it comes in contact with the air zone 27.

In the case of the air flow having a velocity gradient as indicated by the arrows 28, 29 and 30 in Fig. 3, there is produced a decreasing-pressure phenomenon in which the pressure decreases as the predetermined surface 6 of the laminated continuous sheet 2 is approached. This decreasing-pressure phenomenon can be accounted for by Bernoulli's theorem. The decreasing-pressure phenomenon described above in which the pressure decreases as the predetermined surface 6 is approached provides a force which draws the baby powder 13 toward the predetermined surface 6 of the laminated continuous sheet 2, with the result the baby powder 13 adheres to the predetermined surface 6.

The decreasing-pressure phenomenon described above also contributes to transporting the baby powder 13 which is present in the conduit 21. That is, the feed path for the baby powder 13 provided by the conduit 21 is closed except for its connection to the screw feeder 17 and its outlet 22. Further, the connection between the conduit 21 and the screw feeder 17 is blocked by the screw 20 and the baby powder 13 so that there is substantially no air flowing therethrough. For these reasons, if the conduit 21 is positioned to project into the air zone 27 of decreased pressure, the pressure-decreasing state of the air zone 27 extends to the conduit 21 and hence the baby powder 13 is discharged from the outlet 22 not only by natural fall but also by the negative pressure given by the air zone 27. By utilizing this, the delivery rate of the baby powder 13 can be controlled not only by the rotative speed of the screw 20 in the screw feeder 17 but also by the negative pressure appearing at the outlet 22 of the conduit 21, that is, the speed of the air flow shearing across the outlet 22.

The speed of the air flow shearing across the outlet 22 can be changed in the following two manners.

A first manner is to change the distance between the end surface of the outlet 22 and the predetermined surface 6. As can be seen from the velocities of the air flow represented by the arrows 28, 29 and 30, the closer to the predetermined surface 6 the outlet 22 gets, the higher the speed of the air flow shearing across the outlet 22.

A second manner is to change the speed of the laminated continuous sheet 2 traveling in the direction of arrow 3. The higher the traveling speed of the laminated continuous sheet 2, the higher the speed of the air flow shearing across the outlet 22. This means that even if there is a variation in the traveling speed of the laminated continuous sheet 2, the amount of baby powder 13 adhering to the predetermined surface 6 per unit area thereof is kept as constant as possible. That is, to keep constant the amount of baby powder 13 adhering to the predetermined surface 6 per unit area, it is necessary that a greater amount of baby powder 13 be discharged from the outlet 22 when the laminated continuous sheet 2 is traveling at a higher speed and that a smaller amount of baby powder be discharged from the outlet 22 when the laminated continuous sheet 2 is traveling at a lower speed. These requirements can be advantageously met in that any change in the traveling speed of the laminated continuous sheet 2 brings about a change in the amount of baby powder 13 discharged from the outlet.

As shown in FIGS. 1 and 2, in this embodiment, the step of feeding the baby powder 13 to the laminated continuous sheet 2 is performed with the predetermined surface 6 of the laminated continuous sheet 2 directed inward and with the opposite lateral edges 4 and 5 raised. The position to which the baby powder 13 is fed, is the region between the raised opposite lateral edges 4 and 5 of the laminated continuous sheet 2, as can be seen from the positions of the outlets 22 and 22a of the two conduits 21 and 21a. Therefore, the air zone 27 as shown in FIG. 3 is formed on each of the raised opposite lateral edges 4 and 5 of the laminated continuous sheet 2, so that the decreasing pressure phenomenon causes the baby powder 13 to adhere to the predetermined surface 6 on the raised opposite lateral edges 4 and 5.

If the opposite lateral edges 4 and 5 of the laminated continuous sheet 2 have been raised as described above when the baby powder 13 is to be fed, it is possible to minimize the amount of baby powder 13 dispersed into the surroundings and minimize the amount of baby powder 13 wasted to thereby prevent the worsening of the working environment.

As shown in FIG. 1, in this embodiment, immediately after baby powder has been applied to the predetermined surface 6 of the laminated continuous sheet 2, the opposite lateral edges 4 and 5 are bent with the predetermined surface 6 inwardly directed. Thereby, the baby powder can be held adhering to the predetermined surface 6 more effectively. However, if such advantage is not desired, the step of applying baby powder 13 may be performed upstream of the rotary drum 7. It is not essential that the baby powder 13 be fed to the laminated continuous sheet 2 at two positions in the vicinity of the opposite lateral edges 4 and 5, as indicated by the two conduits 21 and 21a in FIGS. 1 and 2. For example, either of the conduits 21 an 21a may be omitted so that the baby powder 13 is fed at one position. Even if the baby powder 13 is fed at one position alone, since the laminated continuous sheet 2 traveling at high speed is bent along the opposite lateral edges 4 and 5, the baby powder 13 once adhering to the laminated continuous sheet 2 is blown off widthwise of the laminated continuous sheet 2 by a relatively strong air current produced during the bending operation, so that the distribution of baby powder 13 can be expected to be leveled off widthwise. In addition, if either of the two conduits 21 and 21a is to be omitted, it is preferable to omit the conduit 21 which is installed adjacent the lateral edge 5 which is to be bent second. The reason is that reversely if the conduit 21a positioned adjacent the lateral edge 4 which is to be bent first is omitted, it is quite within the bounds of possibility that the baby powder 13 applied adjacent the other lateral edge 5 which is to be bent first fails to adhere to the predetermined surface 6 adjacent the lateral edge 4. In addition, in the case where baby powder 13 is applied at one position alone, the conduit therefor may be positioned at the middle of the width of the laminated continuous sheet 2. Further, the outlet corresponding to the outlet 22 of 22a of the conduit 21 or 21a is not limited in shape to a circular cross section as in the illustrated embodiment. For example, a conduit having a slit-like outlet extending widthwise of the laminated continuous sheet 2 may be used. Further, the number of positions at which the baby powder 13 is fed may be three or more.

In the illustrated embodiment, the conduits 21 and 21a have been provided in connection with their respective baby powder applying devices 1; however, they may be designed to branch off from a common baby powder applying device.

As for the method of feeding baby powder 13 at a position within the air zone 27 of predetermined thickness in which an air flow is produced, in such a way that the baby powder contacts the air zone 27, there may be used, besides one using a member such as the conduit 21 or 21, another using a conveying means such as a belt conveyor. In this case, the end of the conveying means such as a belt conveyor is positioned in the air zone so that baby powder contacts the air flow therein.

An important element in this invention is the creation of an air flow in the air zone 27 of predetermined thickness disposed on the predetermined surface 6 of the laminated continuous sheet 2. such air flow will be naturally produced so long as the laminated continuous sheet 2 is traveling at at least a certain speed. However, if the traveling speed of the laminated continuous sheet is low, the thickness of the air zone in which an air flow having a substantial speed is produced is decreased, so that it becomes necessary to bring the outlet of the conduit 21, for example, very close to the predetermined surface 6 of the laminated continuous sheet 2. However, since the laminated continuous sheet 2 tends to vary in thickness and since the smoothness of the surface of the inner member 24, that is, the predetermined surface 6 is low, the outlets 22 and 22a of the conduits 21 and 21a cannot be brought so close to the predetermined surface 6. The reason is that if the outlet 22 or 22a is positioned too close to the predetermined surface 6, this would result in the inner member 24 being caught by the conduit 21 or 21a, decreasing the yield of the product. From such point of view, it is preferable that the thickness of the air zone in which an air flow having a substantial speed is produced be large, and to this end it becomes necessary that the traveling speed of the laminated continuous sheet 2 be high. Practically, the traveling speed of the laminated continuous sheet 2 is 2 m/sec or more.

In addition, it is not necessary that the 'laminated continuous sheet which, when cut, forms individual disposable diapers' so referred to in this specification, has all the structural features required for disposable diapers. For example, such sheet may be a continuous sheet which corresponds to an inner member and which has not yet been laminated to other elements of disposable diapers. Therefore, baby powder 13 may be applied to the absorbent member 25 which is to underlie the inner member 24 and the inner member 24 may then be laminated thereto. In this connection, a laminated continuous sheet also will be referred to as a "laminated continuous sheet which, when cut, forms individual diapers" even if elastic members generally provided in disposable diapers, fasteners for putting diapers on babies and the like have not yet been added to the laminated continuous sheet.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for applying baby powder to disposable diapers comprising the steps of:
    moving a laminated continuous sheet, which, when cut, is to become individual disposable diapers, at high speed in the direction of the length thereof, whereby in an air zone of predetermined thickness disposed on at least a predetermined surface of the laminated continuous sheet, there is produced an air flow having a velocity gradient such that the speed of the air flow increases as said predetermined surface is approached,
    feeding baby powder at a position within said air zone of predetermined thickness in which said air flow is produced, so that the baby powder thus fed contacts said air zone, and
    making use of a decreasing-pressure phenomenon resulting from said air flow having said velocity gradient in which phenomenon the pressure decreases as said predetermined surface is approached, whereby said baby powder is caused to adhere to said predetermined surface of said laminated continuous sheet as it is drawn toward said predetermined surface.

2. A method for applying baby powder to disposable diapers as set forth in claim 1, wherein in said step of feeding baby powder, said baby powder is fed at two positions in the vicinity of the opposite lateral edges of said laminated continuous sheet.

3. A method for applying baby powder to disposable diapers as set forth in claim 1, wherein:
    said step of applying baby powder is performed with said predetermined surface of said laminated continuous sheet inwardly directed and with the opposite lateral edges raised, and
    in said step of feeding baby powder, the position at which said baby powder is fed is a region between said raised opposite lateral edges of said laminated continuous sheet.

4. A method for applying baby powder to disposable diapers as set forth in claim 1, further including the step of bending the opposite lateral edges of said laminated continuous sheet immediately after said step of causing baby powder to adhere has been performed.

5. A method for applying baby powder to disposable diapers as set forth in claim 1, wherein:
    in said step of producing said air flow, the traveling speed of said laminated continuous sheet is 2 m/sec or more.

6. An apparatus for applying baby powder to disposable diapers comprising:
    conveyor means for moving a laminated continuous sheet, which, when cut, is to become individual disposable diapers, at high speed in the direction of the length thereof, whereby in an air zone of predetermined thickness disposed on at least a predetermined surface of the laminated continuous sheet, there is produced an air flow having a velocity gradient such that the speed of the air flow increases as said predetermined surface is approached,
    storage source means for storing baby powder,
    delivery means for delivering said baby powder from said storage source means by a predetermined amount per unit time, and
    feed path means connected to said delivery means for guiding said baby powder delivered therefrom, said feed path means being disposed to extend into said air zone of predetermined thickness in which said air flow is produced, said feed path means having an outlet located in said air zone.

7. An apparatus for applying baby powder to disposable diapers as set forth in claim 6, wherein said storage source means includes a hopper having an opening in the lower end thereof, and said delivery means includes a screw feeder connected to the lower end of said hopper and having a screw adapted to be driven for rotation around a substantially horizontally directed axis.

8. An apparatus for applying baby powder to disposable diapers as set forth in claim 6, wherein said conveyor means conveys said laminated continuous sheet with said predetermined surface directed upward, and said feed path means extends vertically as a whole and having said opening in this lower end.

9. An apparatus for applying baby powder to disposable diapers as set forth in claim 6, further including means for imparting vibration to said storage source means and said delivery means.

10. An apparatus for applying baby powder to disposable diapers as set forth in claim 6, wherein said feed path means is closed except for its connection to said delivery means and its outlet.

* * * * *